(12) United States Patent
Lallier

(10) Patent No.: US 7,737,098 B2
(45) Date of Patent: Jun. 15, 2010

(54) METHOD FOR DISSOLVING OIL AT LOW TEMPERATURE

(75) Inventor: Jean-Pierre Lallier, Saint Bonnet de Mure (FR)

(73) Assignee: Arkema France, Colombes (FR)

( * ) Notice: Subject to any disclaimer, the term of this patent is extended or adjusted under 35 U.S.C. 154(b) by 203 days.

(21) Appl. No.: 11/658,633

(22) PCT Filed: Jul. 18, 2005

(86) PCT No.: PCT/FR2005/001827

§ 371 (c)(1),
(2), (4) Date: Sep. 24, 2008

(87) PCT Pub. No.: WO2006/024728

PCT Pub. Date: Mar. 9, 2006

(65) Prior Publication Data

US 2009/0048138 A1 Feb. 19, 2009

(30) Foreign Application Priority Data

Jul. 29, 2004 (FR) .................................. 04 08363

(51) Int. Cl.
*C11D 7/50* (2006.01)
(52) U.S. Cl. ....................... 510/177; 510/408; 510/411; 510/412
(58) Field of Classification Search ................. 510/177, 510/408, 411, 412; 252/67
See application file for complete search history.

(56) References Cited

U.S. PATENT DOCUMENTS

| 6,951,835 B1 | 10/2005 | Minor et al. |
| 2004/0171510 A1 | 9/2004 | Minor et al. |
| 2005/0267006 A1 | 12/2005 | Minor et al. |

*Primary Examiner*—Gregory E Webb
(74) *Attorney, Agent, or Firm*—Steven D. Boyd

(57) ABSTRACT

The present invention relates to the field of solvents. It relates more particularly to a process for the dissolution of oil at low temperature. Another subject matter of the invention is a novel composition based on 1,1,1,3,3-pentafluorobutane (HFC-365mfc) and on 1,1,1,2,3,4,4,5,5,5-decafluoropentane (HFC-43-10mee).

6 Claims, No Drawings

METHOD FOR DISSOLVING OIL AT LOW TEMPERATURE

FIELD OF THE INVENTION

The present invention relates to the field of solvents. It relates more particularly to a process for the dissolution of oil at low temperature. Another subject-matter of the invention is a novel composition based on 1,1,1,3,3-pentafluorobutane (HFC-365mfc) and on 1,1,1,2,3,4,4,5,5,5-decafluoropentane (HFC-43-10mee).

BACKGROUND OF THE INVENTION

The document WO 00/56833 discloses quasiazeotropic binary compositions composed essentially of 1,1,1,3,3-pentafluorobutane (HFC-365mfc) and 1,1,1,2,3,4,4,5,5,5-decafluoropentane (HFC-43-10mee) or nonafluoromethoxybutane. This document also discloses quasiazeotropic ternary and quaternary compositions composed essentially of 1,1,1,3,3-pentafluorobutane (HFC-365mfc), 1,1,1,2,3,4,4,5,5,5-decafluoropentane (HFC-43-10mee) or nonafluoromethoxybutane and trans-1,2-dichloroethylene (t-DCE), n-propyl bromide, acetone, methanol, ethanol or isopropanol.

Examples 4 and 5 of the document WO 00/56833 describe tests of oil solubility, at ambient temperature, of certain compositions. Thus, a composition comprising 31% by weight of 43-10mee, 31% by weight of 365mfc and 38% by weight of t-DCE was evaluated with a mineral oil (Table 4) and a composition comprising 33% by weight of 43-10mee, 28% by weight of 365mfc and 39% by weight of t-DCE was evaluated with a DC-200 silicone oil (Table 5).

However, the ternary compositions of this document are not effective in applications which require operating at low temperature, such as, for example, in the medical field or other fields.

The inventor has discovered a process for the dissolution of oil at low temperatures.

A first subject-matter of the present invention is a process for the dissolution of oil at low temperature, characterized in that use is made of a composition comprising 1,1,1,3,3-pentafluorobutane (HFC-365mfc), 1,1,1,2,3,4,4,5,5,5-decafluoropentane (HFC-43-10mee), trans-1,2-dichloroethylene (t-DCE) and from 1 to 10% by weight of an alcohol comprising from 2 to 4 carbon atoms.

The process according to the present invention is preferably carried out at a temperature of less than 10° C. A temperature of between 0 and 8° C. is also preferred. A temperature of between 3 and 6° C. is advantageously chosen.

Use is preferably made of a composition comprising from 40 to 69% by weight of a binary mixture comprising 1,1,1,3,3-pentafluorobutane and 1,1,1,2,3,4,4,5,5,5-decafluorobutane, from 30 to 50% by weight of trans-1,2-dichloroethylene and from 1 to 10% by weight of an alcohol comprising from 2 to 4 carbon atoms.

Use is advantageously made of a composition comprising from 45 to 64% by weight of the HFC-365mfc and HFC-43-10mee binary mixture, from 35 to 45% by weight of trans-1,2-dichloroethylene and from 1 to 10% by weight of an alcohol comprising from 2 to 4 carbon atoms.

The amount of alcohol present in the composition is advantageously between 1 and 5% by weight.

Ethanol, propanol, isopropanol, butanol, secondary-butanol (sec-butanol) or tert-butanol may be suitable. Use is preferably made of isopropanol or sec-butanol. sec-Butanol is advantageously preferred.

The 1,1,1,2,3,4,4,5,5,5-decafluoropentane preferably represents at least 17% by weight of the binary mixture.

The process according to the invention is suitable for mineral or silicone oils. This process can be applied to the uniform deposition of oils on a substrate, for example kitchen utensils. It is very particularly suitable for the deposition of silicone oil of medical grade, in particular deposition on medical instruments, such as syringe needles or catheters. This is because silicone oil is used as lubricant for hypodermic medical syringes in order to reduce the pain associated with the insertion of the needle into the skin of the patient.

The process according to the present invention is suitable for the cleaning, degreasing and drying of very diverse solid surfaces (metal components, glass, plastics, composites). It can also be employed in the manufacture of printed circuits for removing the residues of the substances used to improve the quality of the solder joints. This removal operation is denoted in the trade by the term "defluxing".

A second subject-matter of the present invention is a composition comprising 1,1,1,3,3-pentafluorobutane (HFC-365mfc), 1,1,1,2,3,4,4,5,5,5-decafluoropentane (HFC-43-10mee), trans-1,2-dichloroethylene (t-DCE) and from 1 to 10% by weight of an alcohol comprising 4 carbon atoms.

The composition which is particularly preferred according to the second subject-matter of the present invention comprises from 40 to 69% by weight of a binary mixture comprising 1,1,1,3,3-pentafluorobutane and 1,1,1,2,3,4,4,5,5,5-decafluoropentane, from 30 to 50% by weight of trans-1,2-dichloroethylene and from 1 to 10% by weight of an alcohol comprising 4 carbon atoms.

A composition comprising from 45 to 64% by weight of the HFC-365mfc and HFC-43-10mee binary mixture, from 35 to 45% by weight of trans-1,2-dichloroethylene and from 1 to 10% by weight of an alcohol comprising 4 carbon atoms is advantageously preferred.

The amount of alcohol present in the composition is advantageously between 1 and 5% by weight.

sec-Butanol is advantageously chosen as alcohol.

The 1,1,1,2,3,4,4,5,5,5-decafluoropentane preferably represents at least 17% by weight of the binary mixture.

The composition according to the second subject-matter can be used in the industry for cleaning, degreasing and drying very diverse solid surfaces (metal components, glass, plastics, composites). It can also be employed in the manufacture of printed circuits for removing the residues of the substances used to improve the quality of the solder joints. This removal operation is denoted in the trade by the term "defluxing".

In addition, it can be used as blowing agent for polyurethane foams, as aerosol propellant, as heat-exchange fluid, as dry cleaning agent for textiles or as agent for cleaning refrigerating plants.

EXPERIMENTAL PART

Example 1

Description of the Tests of Dissolution of a Silicone Oil

Use is made of a Crompton L9000-1000 silicone oil from Crompton Corporation (Greenwich, USA). It is a transparent liquid hydroxypolydimethyl-siloxane having a density of 0.97 at ambient temperature (22° C.), a boiling point of greater than 200° C. and a flash point of 132° C. (Pensky-Martens closed cup method).

Mixtures are prepared at ambient temperature, that is to say at 22° C.

Thus, 18 ml of the composition based on 365mfc and 43-10mee (to be tested) and 1.94 g of silicone oil are introduced into a 50 ml flask, that is to say that a 10% by volume solution is prepared. The mixture is subsequently stirred manually for 5 minutes.

A portion of the mixture thus prepared is kept standing at ambient temperature (22° C.) for 24 hours. Another portion is kept standing at low temperature (6° C.) for 7 days.

After the period of storage at different temperatures, the appearance of the mixture is closely observed. It is considered that there is solubility at ambient temperature or at 6° C. when the mixture is transparent, clear, homogeneous, single-phase and stable.

The following compositions were prepared:

Composition A: 80% by weight of HFC-365mfc and 20% by weight of HFC-43-10mee

Composition B: 48% by weight of HFC-365mfc and 12% by weight of HFC-43-10mee and 40% by weight of trans-1,2-dichloroethylene Composition C: 44% by weight of HFC-365mfc and 11% by weight of HFC-43-10mee, 40% by weight of trans-1,2-dichloroethylene and 5% by weight of sec-butanol Results

| Composition | Solubility at 22° C. | Solubility at 6° C. |
|---|---|---|
| Composition A | NO | NO |
| Composition B | YES | NO |
| Composition C | YES | YES |

Example 2

Description of the Flammability Test

For the evaluation of the flammability of the compositions, their flash points were determined according to the ASTM D3828 standardized method, Setaflash closed cup. The flash point is the minimum temperature at which the liquid gives off vapours in an amount sufficient to form, at its surface, a mixture which is flammable in air under the action of a source of ignition but without persistence of flames when the activation energy is withdrawn.

For each of the compositions, the measurement was repeated 5 times in order to obtain reliable results.

Results

| Composition | Flash Point |
|---|---|
| Composition A | NO |
| Composition B | NO |
| Composition C | NO |

Example 3

Description of the Measurement of Evaporation Rate

A square-shaped screen of stainless steel with a length per side of 4 cm and with 30 wires per cm is used. This type of screen with a close-packed meshing makes it possible to obtain good retention of the solvent after dipping.

The screen is dipped in a 100 ml beaker containing 80 ml of the test composition maintained at ambient temperature, with controlled and stable ventilation.

A stopwatch which will measure the evaporation rate is started at the moment when the completely immersed screen is withdrawn from the test composition. The end of the evaporation is determined by observing the composition front which migrates over time (at the instant of the end of the evaporation, the front disappears). Approximately fifteen measurements were carried out and the mean value of these measurements is listed in the table below.

Result

| Composition | Evaporation time |
|---|---|
| Composition C | 14 seconds |

The invention claimed is:

1. Process for the dissolution of oil at low temperature, characterized in that use is made of a composition comprising 1,1,1,3,3-pentafluorobutane (HFC-365mfc), 1,1,1,2,3,4,4,5,5,5-decafluoropentane (HFC-43-10mee), trans-1,2-dichloroethylene (t-DCE) and from 1 to 10% by weight of an alcohol comprising from 2 to 4 carbon atoms.

2. Process according to claim 1, characterized in that the temperature is less than 10° C.

3. Process according to claim 1, characterized in that use is made of a composition comprising from 40 to 69% by weight of a binary mixture comprising 1,1,1,3,3-pentafluorobutane and 1,1,1,2,3,4,4,5,5,5-decafluorobutane, from 30 to 50% by weight of trans-1,2-dichloroethylene and from 1 to 10% by weight of an alcohol comprising from 2 to 4 carbon atoms.

4. Process according to claim 3, characterized in that use is made of a composition comprising from 45 to 64% by weight of the HFC-365mfc and HFC-43-10mee binary mixture, from 35 to 45% by weight of trans-1,2-dichloroethylene and from 1 to 10% by weight of an alcohol comprising from 2 to 4 carbon atoms.

5. Process according to claim 1, characterized in that the temperature is between 0 and 8° C.

6. Process according to claim 1, characterized in that the temperature is between 3 and 6° C.

* * * * *